(12) United States Patent
Liu et al.

(10) Patent No.: US 6,448,197 B1
(45) Date of Patent: Sep. 10, 2002

(54) METHOD FOR MAKING A METAL CONTAINING SMALL PORE MOLECULAR SIEVE CATALYST

(75) Inventors: Zhongmin Liu; Lixin Yang; Lei Xu; Chenglin Sun, all of Dalian (CN); Yi-Gang Xiong, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/615,526

(22) Filed: Jul. 13, 2000

(51) Int. Cl.⁷ .................. B01J 29/85; B01J 27/188; B01J 27/185; B01J 27/182
(52) U.S. Cl. .................. 502/210; 502/214; 502/213; 423/DIG. 30
(58) Field of Search .................. 502/208, 210, 502/213, 214, 232, 211; 423/DIG. 30, 327.1, 325

(56) References Cited

U.S. PATENT DOCUMENTS

| | | | |
|---|---|---|---|
| 4,451,572 A | | 5/1984 | Cody |
| 4,692,424 A | | 9/1987 | Le Van Mao |
| 4,814,306 A | * | 3/1989 | Von Ballmoos et al. .... 502/213 |
| 4,859,314 A | | 8/1989 | Pellet et al. |
| 4,861,743 A | * | 8/1989 | Flank et al. ............. 423/305 |
| 4,884,531 A | * | 12/1989 | Degnan et al. ............. 123/3 |
| 4,912,073 A | * | 3/1990 | Chu ...................... 502/214 |
| 5,100,596 A | | 3/1992 | Haag et al. |
| 5,155,075 A | | 10/1992 | Innes et al. |
| 5,158,665 A | | 10/1992 | Miller |
| 5,276,236 A | | 1/1994 | Patton |
| 5,403,800 A | | 4/1995 | Beck et al. |
| 5,516,957 A | | 5/1996 | Dandekar et al. |
| 5,541,146 A | | 7/1996 | Chang et al. |
| 5,545,784 A | | 8/1996 | Weitkamp et al. |
| 5,552,357 A | | 9/1996 | Lago et al. |
| 5,602,066 A | | 2/1997 | Beck et al. |
| 5,817,595 A | | 10/1998 | Tejada et al. |
| 5,849,968 A | | 12/1998 | Beck et al. |
| 5,851,378 A | * | 12/1998 | Vogt et al. .................. 208/111 |
| 5,869,417 A | * | 2/1999 | Woo et al. .................. 502/103 |
| 5,879,655 A | | 3/1999 | Miller et al. |
| 5,916,433 A | | 6/1999 | Tejada et al. |
| 5,962,762 A | | 10/1999 | Sun et al. |
| 6,005,155 A | * | 12/1999 | Sun ........................... 502/85 |
| 6,040,264 A | * | 3/2000 | Sun et al. .................... 423/305 |
| 6,046,373 A | * | 4/2000 | Sun ........................ 204/157.15 |
| 6,127,432 A | * | 10/2000 | Wegman et al. ............. 518/715 |

FOREIGN PATENT DOCUMENTS

WO     WO 91/13132     9/1991

* cited by examiner

Primary Examiner—Wayne A. Langel
Assistant Examiner—Christina Ildebrando

(57) ABSTRACT

A molecular sieve and a molecular sieve catalyst containing a surface heat impregnated with a metal. The molecular sieve is heated in the presence of a metal containing solution at a temperature between 30° C. and 400° C. then separated from the metal containing solution. The molecular sieve and molecular sieve catalyst is used to make olefin from an oxygenate feedstock.

18 Claims, 3 Drawing Sheets

METHOD FOR MAKING A METAL CONTAINING SMALL PORE MOLECULAR SIEVE CATALYST

FIELD OF THE INVENTION

The invention is directed to a method of making molecular sieve that contain metals, catalysts containing molecular sieves that contain metals, and a method for converting an oxygenate feedstock to a product, including olefin. In particular, the invention is directed to a silicoaluminophosphate catalyst with a molecular sieve surface that is heat impregnated with a metal.

BACKGROUND OF THE INVENTION

Olefins, particularly light olefins, have been traditionally produced from petroleum feedstocks by either catalytic or steam cracking. Oxygenates, however, are becoming an alternative feedstock for making light olefins, particularly ethylene and propylene. Promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including synthesis gas derived from natural gas; petroleum liquids; and carbonaceous materials, including coal. Because of the relatively low-cost of these sources, alcohol, alcohol derivatives, and other oxygenates have promise as an economical, non-petroleum source for light olefin production.

One way of producing olefins is by the catalytic conversion of methanol using a silicoaluminophosphate (SAPO) molecular sieve catalyst. For example, U.S. Pat. No. 4,499,327 to Kaiser, discloses making olefins from methanol using a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 $hr^{-1}$.

Inui has shown that nickel substitution into the SAPO-34 framework results in an increase of ethylene selectivity relative to unsubstituted SAPO-34. *J Chemical Society Chem. Commun.* p.205, 1990. For example, at 450° C. the product stream comprised 88% ethylene and 5% propylene (100% methanol conversion).

In contrast to the work of Kaiser and Inui, metal incorporation may also take place post-synthesis, that is, following the synthesis of the molecular sieve framework. For example, U.S. Pat. No. 5,962,762 to Sun et al. teaches a process for converting methanol to light olefins using a metal-incorporated SAPO catalyst. An aqueous metal solution, preferably a nickel or cobalt containing solution, was adsorbed onto the SAPO molecular sieve by allowing the solution to remain in contact with the SAPO overnight at ambient conditions. The treated molecular sieve was then separated from the solution and dried. U. S. Pat. Nos. 5,625,104 and 5,849,968 to Beck at al. teach a process of incorporating alkali earth and alkaline earth metals into a zeolitic catalyst by pretreating the zeolite with an organo-silicon or poly-oxo silicon compound followed by the treatment of a metal solution. U.S. Pat. No. 4,692,424 to Le Van Mao teaches a process for the dry incorporation of manganese ions on the external reactive sites of ZSM catalysts by adding a minimum amount of an aqueous manganese solution to form a malleable paste and extruding the paste under pressure.

In spite of the prior efforts to modify molecular sieve, the need to find a molecular sieve or molecular sieve catalyst that exhibits high ethylene and/or propylene selectivity still exists. Otherwise, the use of crude oil feedstock to produce these olefins will continue to be economically favored.

SUMMARY OF THE INVENTION

This invention provides various compositions of a molecular sieve having a surface heat impregnated with one or more metals and of a method of making the same. The metals are selected from Group IIA metals, Group IHA metals, Group IB metals, Group 111 metals, Group 111 metals, Group VIB metals, Group VB metals, Group VIIB metals, Group VIIIB metals, Group VI11B metals, and mixtures thereof.

In one embodiment, the metals are selected from aluminum, magnesium, calcium, barium, lanthanum, titanium, chromium, iron, cobalt, nickel, copper, zinc, and mixtures thereof The silicoaluminophosphate (SAPO) molecular sieve will contain about 0.5 to 40 percent by weight, preferably about 1 to 20 percent by weight, most preferably 1 to 10 percent by weight, of the metal. In the preferred embodiment, the SAPO molecular sieve will have a surface heat impregnated with copper, zinc, or a mixture thereof, wherein the copper and/or zinc will be present in about 1 to 20 percent by weight. The metal disposed on the SAPO molecular sieve is a heat decomposition product of a metal acetate, metal nitrate, metal sulfate, or metal halide. The surface is heat impregnated with the metal at a temperature from 30° C. to 400° C., preferably from 120° C. to 260° C., most preferably from 160° C. to 220° C. The SAPO molecular sieve is selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO47, SAPO-56, the metal containing forms thereof, and mixtures thereof, more preferably, SAPO-18, SAPO-34, SAPO-35, SAPO-44, SAPO-47, and mixtures thereof, most preferably, SAPO-34A, SAPO-34B, and mixtures thereof.

The invention is also directed to a SAPO molecular sieve catalyst comprising: a surface heat impregnated with a metal selected from the group consisting of Group IIA metals, Group IHA metals, Group IB metals, Group IIB metals, Group IIIB metals, Group VIB metals, Group VB metals, Group VIB metals, Group VIIB metals, Group VIIIB metals, and mixtures thereof; and a binder. Generally, the binder is selected from alumina, aluminum chlorhydrol, clay, and mixtures thereof.

In one embodiment, the metals are selected from aluminum, magnesium, calcium, barium, lanthanum, titanium, chromium, iron, cobalt, nickel, copper, zinc, and mixtures thereof. The SAPO molecular sieve will have about 0.5 to 40 percent by weight, preferably about 1 to 20 percent by weight, most preferably 1 to 10 percent by weight, of the metal. In the preferred embodiment, the SAPO molecular sieve will have a surface heat impregnated with copper, zinc, or a mixture thereof, wherein the copper and/or zinc will be present in about 1 to 20 percent by weight. The metal disposed on the SAPO molecular sieve is a heat decomposition product of a metal acetate, metal nitrate, metal sulfate, or metal halide. The surface is heat impregnated with the metal at a temperature from 30° C. to 400° C., preferably from 120° C. to 260° C., most preferably from 160° C. to 220° C. The SAPO molecular sieve is selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO40, SAPO-41, SAPO-42, SAPO-44, SAPO-47, SAPO-56, the metal containing forms thereof, and mixtures thereof, more preferably, SAPO-18, SAPO-34, SAPO-35, SAPO-44, SAPO-47, and mixtures thereof, most preferably, SAPO-34A, SAPO-34B, and mixtures thereof.

The invention is also directed to a method of making a molecular sieve comprising: mixing a metal containing solution with a SAPO molecular sieve, wherein the SAPO molecular sieve contains a template; heating the mixture to a temperature between 30° C. and 400° C. to obtain a SAPO molecular sieve having a surface heat impregnated with a metal; separating the heated SAPO molecular sieve from the heated metal containing solution; and calcining the separated SAPO molecular sieve. The metal is selected from the group consisting of Group IIA metals, Group IIA metals, Group IB metals, Group IIB metals, Group IIIB metals, Group VIB metals, Group VB metals, Group VIB metals, Group VIIB metals, Group VIIIB metals, and mixtures thereof In one embodiment, the metal is selected from aluminum, magnesium, calcium, barium, lanthanum, titanium, chromium, iron, cobalt, nickel, copper, zinc, and mixtures thereof, more preferably copper, zinc, or a mixture thereof The source of the metal is the heat decomposition product of the metal containing solution. In one embodiment, selected metal salts include acetates, nitrates, sulfates, halides, and mixtures thereof, more preferably nitrates. The metal containing solution comprises a metal concentration between 0.01 M and 1.0 M, preferably between 0.05 M and 0.5 M, more preferably between 0.08 M and 0.3 M. The surface heat impregnated with the metal is heat impregnated at a temperature from 30° C. to 400° C., preferably from 120° C. to 260° C., more preferably from 160° C. to 220° C., at autogeneous pressure.

The invention is also directed to a method of making an olefin from an oxygenate feedstock comprising: providing a catalyst comprising a SAPO molecular sieve having a surface heat impregnated with a metal selected from the group consisting of Group IIA metals, Group IHA metals, Group IB metals, Group IIB metals, Group IIIB metals, Group VIB metals, Group VB metals, Group VIB metals, Group VIIB metals, Group VIIIB metals, mixtures thereof, and a binder; and contacting the oxygenate feedstock with the catalyst.

In one embodiment, the SAPO molecular sieve is selected from SAPO-18, SAPO-34, SAPO-35, SAPO-44, SAPO47, and mixtures thereof In the preferred embodiment, the SAPO molecular sieve has a surface heat impregnated with a metal comprising copper, zinc, or a mixture thereof. The copper, zinc, or a mixture thereof is present in the molecular sieve in about 1 to 20 percent by weight. The preferred oxygenate feedstock will comprise methanol.

BRIEF DESCRIPTION OF THE DRAWINGS

The present invention will be better understood by reference to the Detailed Description of the Invention when taken together with the attached drawings, wherein.

DETAILED DESCRIPTION OF THE INVENTION

Figure 1:
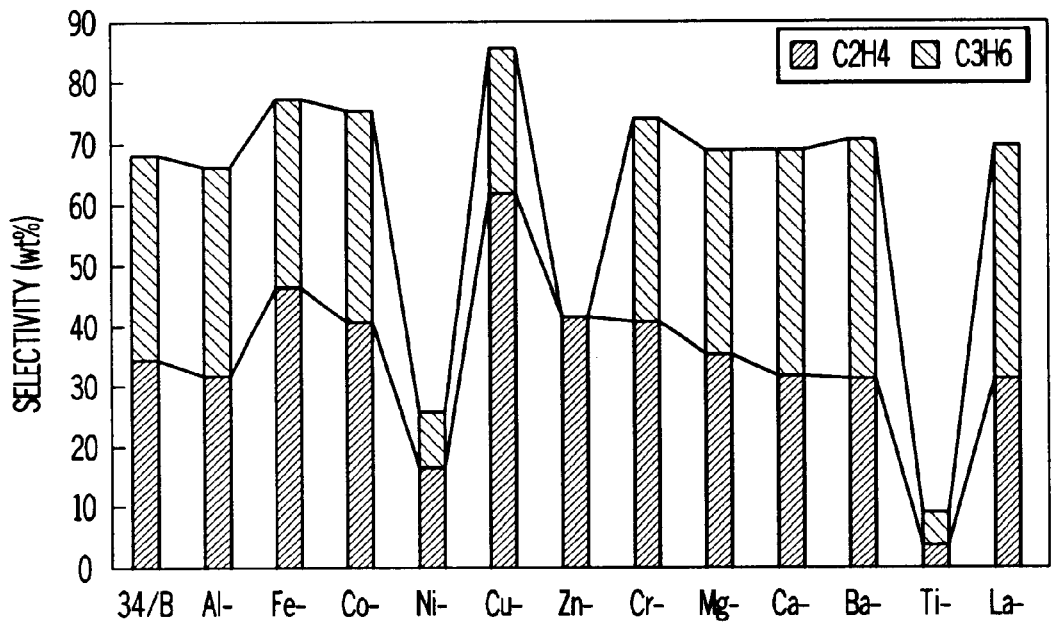
FIG. 1 is a graphical representation of ethylene and propylene selectivity of a heat impregnated metal SAPO-34A with a process temperature of approximately 200° C.

This invention is to a molecular sieve and a catalyst containing the molecular sieve in which the surface of the molecular sieve has been heat impregnated with a metal. The molecular sieve and catalyst of the invention offer significant improvement in the amount of ethylene produced from an oxygenate feedstock.

The molecular sieve of this invention is preferably a silicoaluminophosphate (SAPO) molecular sieve. This type of molecular sieve comprises a three-dimensional microporous crystal framework structure of $[SiO_2]$, $[AlO_2]$ and $[PO2]$ corner sharing tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\delta(Si)$ in the range of −88 to −96 ppm and with a combined peak area in that range of at least 20% of the total peak area of all peaks with a chemical shift $\delta(Si)$ in the range of −88 ppm to −115 ppm, where the $\delta(Si)$ chemical shifts refer to external tetramethylsilane (TMS).

It is preferred that the SAPO molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

SAPO molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

In general, SAPO molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AMO_2]$ tetrahedral units within the framework structure can be provided by a variety of compositions. Examples of these aluminum-containing icompositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeSAPOs or metal-containing silicoaluminophosphates. The metal can be alkali metal ions (Group IA), alkaline earth metal ions (Group IIA), rare earth ions (Group IIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition metals of Groups IVB, VB, VIB, VIB, VIIIB, IB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve.

Suitable SAPO molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof Preferred are SAPO-18, SAPO-34, SAPO-35, SAPO-44, and SAPO-47, particularly SAPO-34, including the metal containing forms thereof, and mixtures thereof As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an AlPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of MO$_2$, AlO$_2$ and PO$_2$ tetrahedral units. These as manufactured structures (which contain template prior to calcination) can be represented by empirical chemical composition, on an anhydrous basis, as:

mR:(M$_x$Al$_y$P$_z$)O$_2$ wherein "R" represents at least one organic templating agent present in the intracrystalline pore system; "m" represents the moles of "R" present per mole of (M$_x$Al$_y$P$_z$)O$_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The SAPO molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product is formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be partly or completely removed for the molecular sieve to exhibit optimal catalytic activity. Once the template is removed or partially removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof Preferred templates are triethylamine, cyclohexylamine, piperidine, pyridine, isopropylamine, tetraethyl ammonium salts, dipropylamine, and mixtures thereof The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate. Particularly preferred templates are diethylamine (DEA) as used in the preparation of SAPO-34A and triethylamine (TEA), as used in the preparation of SAPO-34B.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The SAPO molecular sieve of the invention can be admixed (i.e., blended, formulated) with other materials. Once prepared, the resulting composition is typically referred to as a SAPO catalyst, with the catalyst comprising the SAPO molecular sieve. Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, aluminum chlorhydrol, titania, zirconia, magnesia, thoria, beryllia, quartz, silica or silica or silica sol, and mixtures thereof These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Preferably an alumina binder such as aluminum chlorhydrol, and/or one or more clays, such as kaolin, is used in combination with the molecular sieve of the invention. If the molecular sieve is in the dry from, a fluid, such as water, is added to form a slurry. More often, however, the catalyst is prepared following the preparation of the molecular sieve which is maintained as a slurry from the preceding crystallization step. The other components are then added to the slurried molecular sieve as either dry solids and/or as slurries. This final slurry having a specific solid content and particle size is mixed until a relatively uniform distribution of all components is obtained. The uniformly mixed slurry is then spray dried or extruded to form the catalyst.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CFH, DAC, DDR, EDI, ERI, GOO, KFI, LEV, LOV, LTA, MON, PAU, PHI, RHO, ROG, THO, and substituted forms thereof Structural types of medium pore molecular sieves that are suitable for use in this invention include MFI, MEL, MTW, EUO, MTT, HEU, FER, AFO, AEL, TON, and substituted forms thereof These small and medium pore molecular sieves are described in greater detail in the *Alias of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

Incorporating the metal after the molecular sieve has been prepared has some advantages over that of in-situ metal incorporation. The physical characteristics of the molecular sieve, such as particle and pore size, can be varied prior to metal incorporation. As a result, post-synthesis techniques provide wider possibilities in molecular sieve preparation and screening. For example, a particular metal can be tested over a wide variety of molecular sieve, or a particular molecular sieve can be tested over a wide range of metals.

The molecular sieve of the invention includes a surface heat impregnated with a metal. The source of the metal is a solution of a metal complex. Generally if the solution is aqueous, then the metal complex will comprise metal acetates, nitrates, sulfates, and mixtures thereof. Preferably, metal nitrates are used with the exception of titanium where titanium sulfate is used. If the solution is nonaqueous, such as an alcohol or a polar organic solvent, metal halides can be used. The metal containing solution is then mixed with the molecular sieve in a reaction vessel and heated to the selected temperature. Preferably, the mixture is heated at autogeneous pressure. Typically, the mixture is heated for about 12 hours. However, any period of time can be used depending upon the process temperature, the type of metal complex used, the concentration of the metal solution, and the type of molecular sieve used. It is to be understood that one of ordinary still in the art will know how to vary the amount of time the mixture is heated depending upon each of these parameters.

Following heating of the mixture, the molecular sieve with the surface heat impregnated with the metal is separated from the heated solution. Often the relatively high process temperatures will cause some decomposition of the metal complexes in solution resulting in finely precipitated metals. The separated molecular sieve is then washed with one or more fluids, typically water or an alcohol to remove traces of the metal solution and loosely bound precipitated metal. The washed molecular sieve is dried at 110° C. preferably overnight.

At this point the molecular sieve of the invention can be described as having a surface heat impregnated with a metal. The metal can be disposed on the external surface and/or within the pores of the molecular sieve. Initially, the molecular sieve that is mixed with the metal containing solution had its template positioned within the pore structure. However, as the process temperature is raised the template can exist the pore structure. The template may have some solubility in the metal containing solution, thus enabling the metal complex to replace the template in the pores. Often the process temperature is above the boiling or melting point of the template molecule even at the elevated pressures of the heating process. Alternatively, the high process temperature can initiate decomposition mechanisms of the template. For example during calcination conditions, DEA and TEA are known to form ethylene and water as they thermally decompose. The decomposed products can then exit the pores. However, the pathway, usually some or all of the template will exit the pore during heating and be replaced with the metal and/or metal complex.

After the metal containing molecular sieve is washed and dried, the molecular sieve can be calcined or partially calcined under various conditions. Typically, the molecular sieve of the invention is calcined at 550° C. in air for about 2 to 5 hours prior to use in a conversion reactor.

The surface of the molecular sieve can also be impregnated with additional metals by adding a co-solution of the desired co-metal. Alternatively, the surface of the molecular sieve can be impregnated with the additional co-metal by following the first heat treatment with one or more subsequent heat treatments. For example, proportional amounts of cobalt and/or zinc can be added to SAPO with a surface impregnated with copper according to the invention by adding a cobalt and/or zinc solution to the Cu-SAPO and repeating the heating step.

The catalyst composition preferably comprises about 1% to about 99%, more preferably about 5% to about 90%, and most preferably about 10% to about 80%, by weight of molecular sieve. It is also preferred that the catalyst composition have a particle size of from about 20 $\mu$ to 3,000 $\mu$, more preferably about 30 $\mu$ to 200 $\mu$, most preferably about 50 $\mu$ to 150 $\mu$.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof In this invention, a feed containing an oxygenate, and optionally a diluent or a hydrocarbon added separately or mixed with the oxygenate, is contacted with a catalyst containing a SAPO molecular sieve in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a reactor is defined herein as "feedstock exposed." Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

At any given instant in time, some of the catalyst in the reactor will be fresh, some regenerated, and some coked or partially coked as a result of having not yet been regenerated. Therefore, various portions of the catalyst in the reactor will have been feedstock exposed for different periods of time. Since the rate at which feed flows to the reactor can vary, the amount of feed to which various portions of the catalyst can also vary. To account for this variation, the "average catalyst feedstock exposure index (ACFE index)" is used to quantitatively define the extent to which the entire catalyst in the reactor has been feedstock exposed.

As used herein, ACFE index is the total weight of feed divided by the total weight of molecular sieve (i.e., excluding binder, inerts, etc., of the catalyst composition) sent to the reactor. The measurement should be made over an equivalent time interval, and the time interval should be long enough to smooth out fluctuations in catalyst or feedstock rates according to the reactor and regeneration process step selected to allow the system to be viewed as essentially continuous. In the case of reactor systems with periodic regenerations, this can range from hours up to days or longer. In the case of reactor systems with substantially constant regeneration, minutes or hours may be sufficient.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used. Many such techniques are described, for example, by Michel Louge, "Experimental Techniques," Circulating Fluidized Beds, Grace, Avidan, & Knowlton, eds., Blackie, 1997 (336–337), the descriptions of which are expressly incorporated herein by reference.

In this invention, only the molecular sieve in the catalyst sent to the reactor may be used in the determination of ACFE index. The catalyst sent to the reactor, however, can be either fresh or regenerated or a combination of both. Molecular sieve which may be recirculated to and from the reactor within the reactor apparatus (i.e., via ducts, pipes or annular regions), and which has not been regenerated or does not contain fresh catalyst, is not to be used in the determination of ACFE index.

In a preferred embodiment of this invention, a feed containing an oxygenate, and optionally a hydrocarbon, either separately or mixed with the oxygenate, is contacted with a catalyst containing a SAPO molecular sieve at process conditions effective to produce olefins in a reactor.

Any standard reactor system can be used, including fixed bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to 1000 $hr^{-1}$, and most preferably in the range of from about 20 $hr^{-1}$ to 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to product may result depending upon the catalyst and reaction conditions.

The process can generally be carried out at a wide range of temperatures. An effective operating temperature range can be from about 200° C. to 700° C., preferably from about 300° C. to 600° C., more preferably from about 350° C. to 550° C. At the lower end of the temperature range, the formation of the desired olefin products may become markedly slow. At the upper end of the temperature range, the process may not form an optimum amount of product.

It is highly desirable to operate at a temperature of at least 300° C. and a Temperature Corrected Normalized Methane Sensitivity (TCNMS) of less than about 0.016. It is particularly preferred that the reaction conditions for making olefin from oxygenate comprise a WHSV of at least about 20 $hr^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

The conversion of oxygenates to produce light olefins may be carried out in a variety of catalytic reactors. Reactor types include fixed bed reactors, fluid bed reactors, and concurrent riser reactors as described in "Free Fall Reactor," Fluidization Engineering, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor", Fluidization and Fluid-Particle Systems, pages 48–59, F. A. Zenz and D. F. Othmo, Reinhold Publishing Corp., NY 1960, the detailed descriptions of which are also expressly incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of 250–700° C., desirably in the range of 350–700° C. Preferably, regeneration is carried out at a temperature range of 450–700° C.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred that the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst. Any amount of fresh catalyst can be added, but it is preferred that an ACFE index of at least 1.5 be maintained.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1.

SAPO-34A was made hydrothermally using diethylamine (DEA) as the templating agent. SAPO-34A, 10 grams, was added to an aqueous zinc nitrate solution, 100 ml, 0.1 M. This mixture was stirred in a 200 ml stainless steel vessel. The vessel was closed and heated in an oven at 180° C. at autogeneous pressure for 12 hours. The molecular sieve was recovered by filtration, washed with water, and dried at 110° C. overnight. The molecular sieve was then calcined by heating in air to 550° C. for two to five hours. This prepared molecular sieve is labeled as Zn-SAPO-34A-180.

EXAMPLE 2.

The procedure of Example 1 was repeated with the exception that the processing temperature was 200° C. This prepared molecular sieve is labeled as Zn-SAPO-34A-200.

EXAMPLE 3.

The procedure of Example 1 was repeated for the other metals listed in Tables 1–5 at the stated processing temperatures and molecular sieve type. In all cases metal nitrates were used, except for M=Ti, where titaniuim sulfate was used.

EXAMPLE 4.

Conversion reactions in which methanol (MeOH) was converted to olefin product was carried out in a fixed bed reactor (ID=½" quartz) with continuous flow of MeOH vapor (WHSV=2hr$^{-1}$) diluted with nitrogen (60 ml/min) at 450° C. The molecular sieve as prepared in Examples 1–3 were pressed into tablets. The prepared tablets were then crushed to a powder with 20–40 mesh size. 1.28 g of the powdered molecular sieve was placed in the reactor and activated at 500° C. in flowing $N_2$ (60 ml/min) for one hour prior to initiating the MeOH feed. The reaction products were analyzed using an on-line gas chromatograph equipped with a Paropak-QS® column and a thermalcouple detector. The test results shown in Tables 1–5 summarize the initial performance of the molecular sieve of the invention approximately two minutes after MeOH was introduced. The relative crystallinity of a given sample was determined using x-ray diffraction, with the non-metal SAPO-34A as the reference sample. The lifetime (min.) is defined as the time-on-stream when MeOH conversion dropped below 100%.

As shown by the product selectivities summarized in Tables 1–5 and depicted graphically in the corresponding FIGS. 1–5, the temperature at which the mixture is heated affects the surface properties, and hence the surface composition of the molecular sieve or at least the way in which the metal is disposed on the molecular sieve surface.

Figure 2:
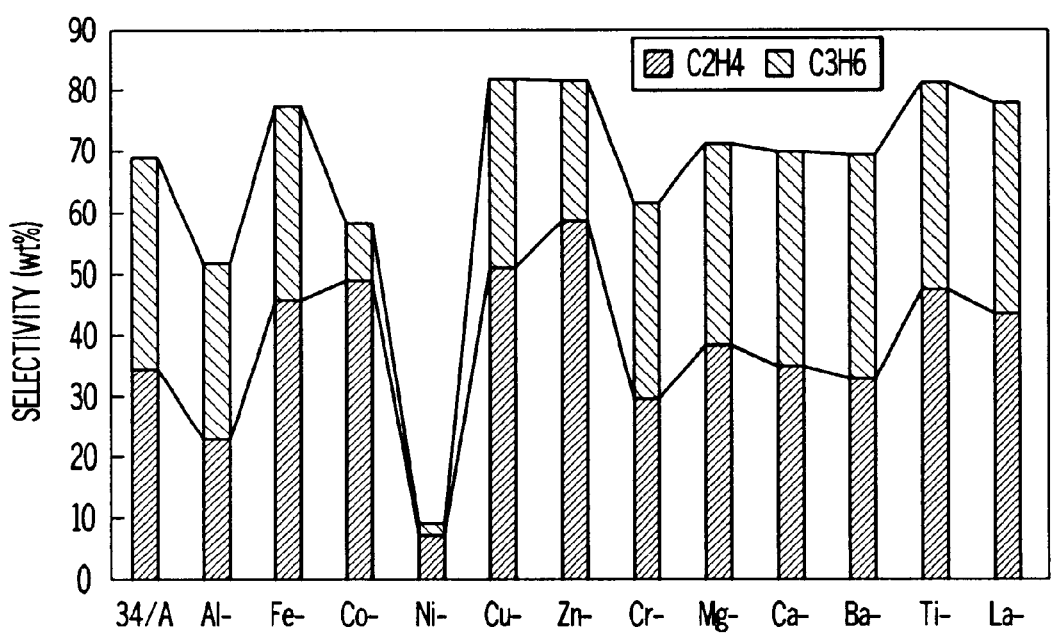
FIG. 2 is a graphical representation of ethylene and propylene selectivity of a heat impregnated metal SAPO-34A with a process temperature approximately 180° C.)

Tables 1 and 2 summarize the methanol-to-olefin (MTO) selectivity to light olefins and other conversion products for the molecular sieve SAPO-34A having a surface heat impregnated with a selected metal. FIGS. 1 and 2 depict a graphical representation of the ethylene and propylene data of Tables 1 and 20, respectively. SAPO-34A without metal present was used as a control for the experiments. As shown, some of the metal molecular sieve of the invention prepared at a temperature of 180° C. exhibited less light olefin selectivity than the control. However, if the process temperature of the invention is increased from 180° C. to 200° C. many of the metal molecular sieve of the invention exhibit higher selectivities than the control. For example, SAPO-34A with a surface heat impregnated with aluminum, cobalt, and chromium exhibits approximately a 15% increase in $C_2$–$C_3$ (ethylene/propylene) olefin selectivity as the processing temperature is increased from 180° C. to 200° C. In contrast, other metals, such as zinc and titanium, exhibit substantially lower levels of $C_2$–$C_3$ selectivity as the temperature is increased. In particular, zinc exhibits decreased levels of approximately 50% and titanium of approximately 90%. At a processing temperature of 180° C. copper and zinc SAPO-34A exhibit very similar $C_2$–$C_3$ selectivities, 81.7% and 81.2%, respectively, though the relative ethylene to propylene ratios are significantly different in the two samples. The Zn-SAPO-34A-180 exhibits a greater selectivity for ethylene, than that of Cu-SAPO-34A-180. However, Cu-SAPO-34A-200 exhibits the highest light olefin selectivity (86%) of any of the molecular sieve of the invention tested to date.

Figure 3:
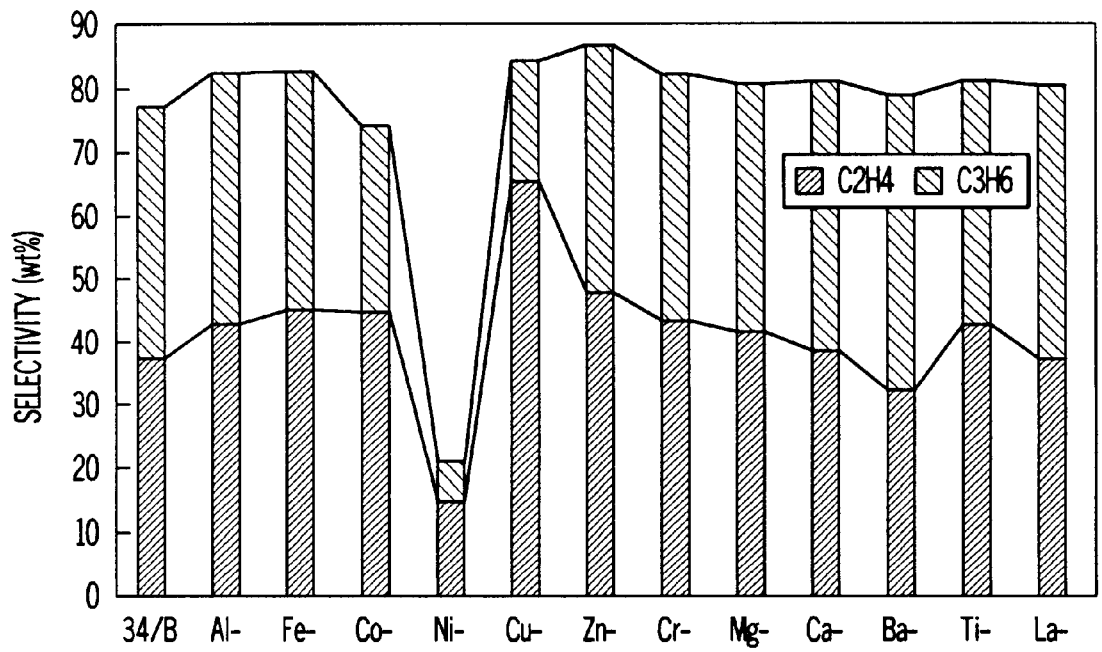
FIG. 3 is a graphical representation of ethylene and propylene selectivity of a heat impregnated metal SAPO-34A with a process temperature approximately 200° C.)
Figure 4:
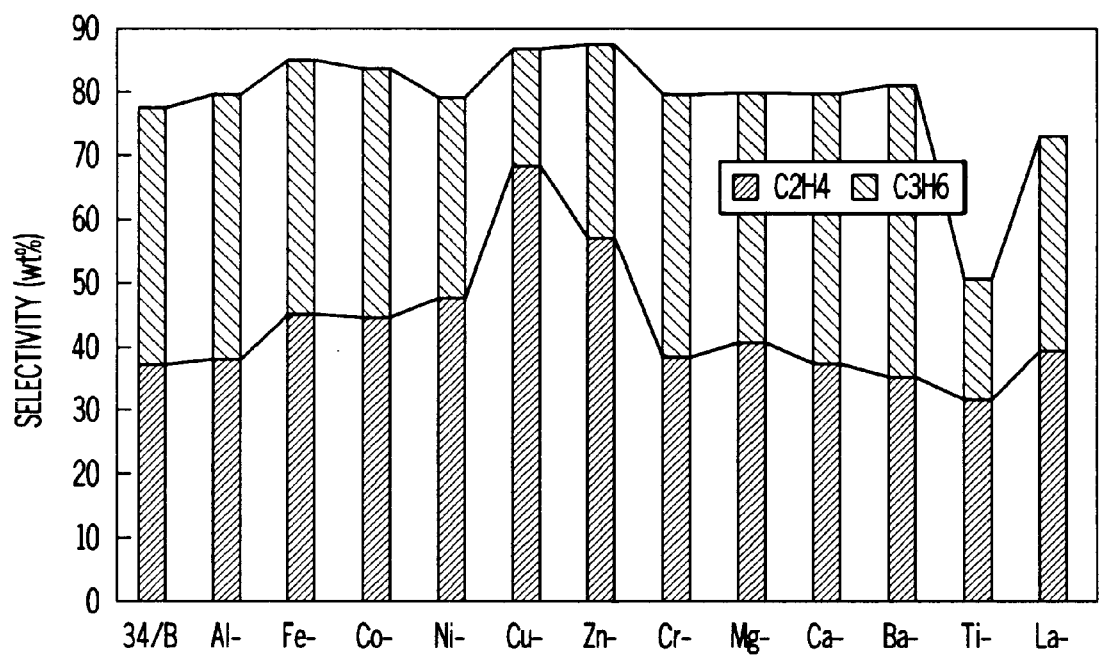
FIG. 4 is a graphical representation of ethylene and propylene selectivity of a heat impregnated metal SAPO-34A with a process temperature approximately 180° C.)
Figure 5:
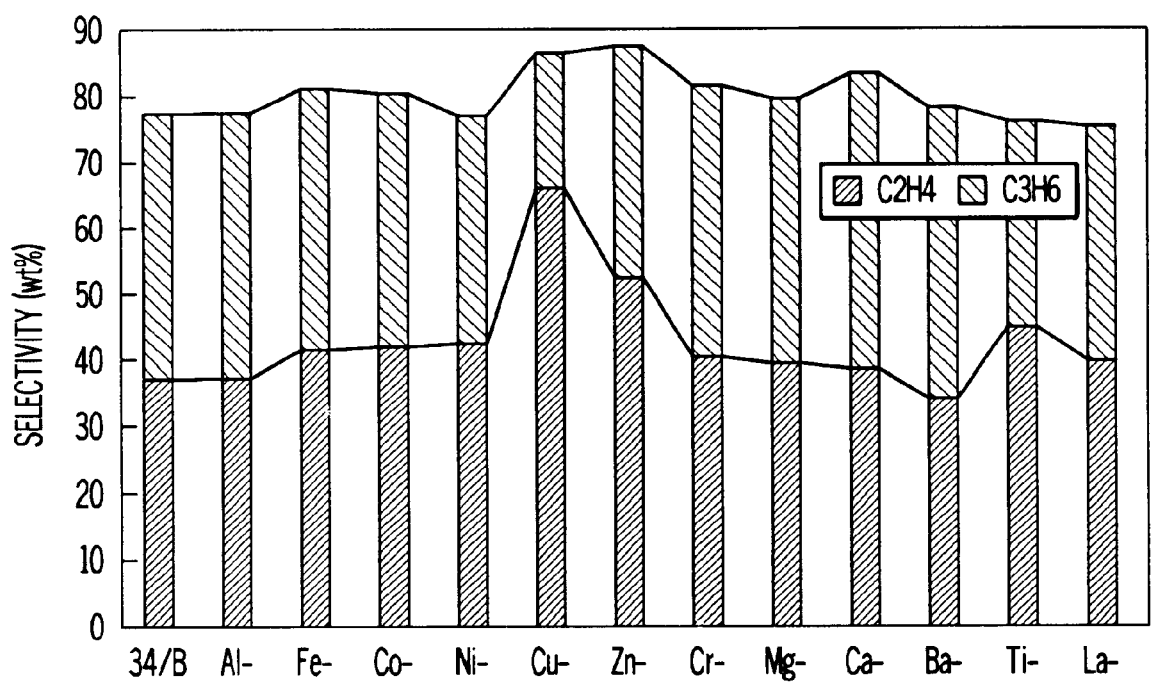
FIG. 5 is a graphical representation of ethylene and propylene selectivity of a heat impregnated metal SAPO-34A with a process temperature approximately 160° C.).

Tables 3–5 summarize the MTO selectivity to light olefins and other products for SAPO-34B having a surface heat impregnated with a metal at 200° C., 180° C. and 160° C., respectively. FIGS. 3–5 depict a graphical representation of the ethylene and propylene data of Tables 3–5, respectively. As shown in Table 5 and the corresponding FIG. 5, the SAPO-34B of the invention prepared at a processing temperature of 160° C. exhibit very little change from the unmodified catalyst with the exception of copper and zinc. However, as the process temperature is increased many of the SAPO-34B of the invention exhibit an increase in ethylene selectivity. Generally, more pronounced increases in ethylene selectivities (3–7%) are observed for SAPO-34B than the corresponding SAPO-34A of the invention. As shown, SAPO-34B with a surface heat impregnated with copper and zinc exhibit the highest degree of light olefin selectivity, particularly ethylene selectivity. One interesting exception to the series SAPO-34B of the invention is barium and calcium SAPO-34B. The SAPO-34B with these two metals exhibit a slight preference for propylene over ethylene.

Depending upon the process temperature Cu-SAPO-34A-T exhibited on average a 20% to 30% increase in ethylene selectivity compared to the control with the added ethylene selectivity coming at the expense of the amount of propylene produced. Also, it is important that the Cu-SAPO-34B-T produces 8 to 10% less $C_3$–$C_5$ paraffin product. Therefore, about two-thirds of the increase in ethylene selectivity comes at the expense of propylene, and the remaining 10% at the expense of undesirable parafin product. The Zn-SAPO-34B-T catalyst exhibited a 10% to 25% increase in ethylene with less of a decrease in propylene. Also, Zn-SAPO-34B-T produced less $C_4^+$ hydrocarbon. Particularly, Zn-SAPO-34B180 exhibits a 24% increase in ethylene selectivity compared to the control. Again, the higher ethylene selectivity comes at the expense of propylene (about 13%), propane (6%) and $C_{5+}$ (4%). As shown in FIGS. 3 and 5 SAPO-34B having a surface heat impregnated with zinc tends to be more dependant upon the process temperature than the corresponding copper molecular sieve of the invention. For example, Zn-SAPO-34B-160 exhibits a 15% increase in ethylene and only a 5% decrease in propylene, while Zn-SAPO-34B-200 exhibits a 10% increase in ethylene with no appreciable loss of propylene selectivity.

Having now fully described this invention, it will be appreciated by those skilled in the art that the invention can be performed within a wide range of parameters within what is claimed, without departing from the spirit and scope of the invention:

TABLE 1

MTO Ions Modification on SAPO-34A-200.

| etal | 34/A | Al— | Fe— | Co— | Ni— | Cu— | Zn— | Cr— | Mg— | Ca— | Ba— | Ti— | La— |
|---|---|---|---|---|---|---|---|---|---|---|---|---|---|
| Relative Crystallinity (%) | 100 | 70 | 32 | 12 | 47 | 57 | 0 | 37 | 95 | 66 | 20 | 0 | 15 |
| Reaction Conditions | | | | | | | | | | | | | |
| Reaction Temp. (° C.) | 460 | 458 | 450 | 460 | 458 | 450 | 455 | 460 | 45 | 455 | 460 | 450 | 465 |
| Reaction Time (min.) | 2 | 2 | 3 | 2 | 2 | 2 | 2 | 2 | 2 | 2 | 2.5 | 2 | 2 |
| Conversion (%) | 100 | 100 | 100 | 100 | 100 | 100 | 1.63 | 100 | 100 | 100 | 100 | 22.1 | 100 |
| Product Distribution (wt %) | | | | | | | | | | | | | |
| $CH_4$ | 1.03 | 1.29 | 3.08 | 1.82 | 56.61 | 3.39 | 55.33 | 1.76 | 1.73 | 1.38. | 1.94 | 89.8 | 0.96 |
| $C_2H_4$ | 34.3 | 31.4 | 46.9 | 41.0 | 16.5 | 62.4 | 41.7 | 40.9 | 35.5 | 32.2 | 32.0 | 3.71 | 31.5 |
| $C_2H_6$ | 1.45 | 1.82 | 2.00 | 0.71 | 8.40 | 1.63 | 0 | 1.38 | 1.38 | 0.78 | 0.84 | 1.08 | 0.98 |
| $C_3H_6$ | 34.0 | 34.9 | 30.5 | 34.9 | 9.46 | 24.0 | 0 | 33.9 | 33.0 | 37.1 | 38.9 | 4.69 | 38.4 |
| $C_3H_8$ | 9.95 | 10.3 | 5.50 | 3.41 | 2.94 | 2.36 | 0 | 6.0 | 7.6 | 7.0 | 7.0 | 0 | 0 |
| $C_4H_8$ | 10.5 | 13.2 | 1.35 | 11.0 | 3.02 | 5.28 | 0 | 10.5 | 13.0 | 13.1 | 11.6 | 0.59 | 14.5 |
| $C_4H_{10}$ | 1.99 | 2.43 | 1.55 | 2.01 | 0.56 | 0.98 | 0 | 1.96 | 2.4 | 2.4 | 2.1 | 0.10 | 2.7 |
| $C_5+$ | 4.51 | 4.66 | 1.96 | 4.14 | 2.47 | 0 | 0 | 3.56 | 5.0 | 6.0 | 5.6 | 0 | 10.6 |
| $C_2=$–$C_3=$ Selectivity (wt %) | 65.3 | 66.3 | 77.6 | 75.9 | 26.0 | 86.3 | 41.7 | 74.8 | 68.8 | 69.4 | 70.9 | 8.4 | 69.9 |
| Lifetime (min.) | 40 | 45 | 45 | 32 | 49 | 34 | <2 | 29 | 75 | 57 | 36 | <2 | .56 |

TABLE 2

MTO Metal Modification on SAPO-34A-180.

| Metal | 34/A | Al— | Fe— | Co— | Ni— | Cu— | Zn— | Cr— | Mg— | Ca— | Ba— | Ti— | La— |
|---|---|---|---|---|---|---|---|---|---|---|---|---|---|
| Relative Crystallinity (%) | 100 | 65 | 39 | 50 | 81 | 50 | 87 | 43 | 104 | 72 | 41 | 23 | 11 |
| Reaction Conditions | | | | | | | | | | | | | |
| Reaction Temp. (° C.) | 460 | 450 | 450 | 460 | 450 | 450 | 455 | 450 | 457 | 450 | 450 | 450 | 453 |
| Reaction Time (min.) | 2 | 2 | 2.5 | 2 | 2.3 | 3 | 2.4 | 2.2 | 2.4 | 2.4 | 22 | 2 | 2.5 |
| Conversion (%) | 100 | 100 | 100 | 100 | 100 | 100 | 100 | 100 | 100 | 100 | 100 | 11.0 | 100 |
| Product Distribution (wt %) | | | | | | | | | | | | | |
| $CH_4$ | 1.03 | 1.60 | 1.66 | 9.74 | 53.9 | 1.99 | 3.5 | 1.7 | 1.0 | 1.2 | 1.2 | 9.9 | 1.0 |
| $C_2H_4$ | 34.3 | 23.0 | 45.3 | 48.4 | 7.4 | 50.4 | 57.9 | 29.6 | 38.2 | 34.5 | 32.4 | 46.6 | 42.5 |
| $C_2H_6$ | 1.45 | 3.00 | 1.65 | 7.17 | 30.7 | 1.17 | 1.7 | 2.0 | 1.3 | 0.87 | 0.78 | 3.8 | 1.2 |
| $C_3H_6$ | 34.0 | 28.2 | 31.8 | 9.71 | 1.8 | 31.3 | 23.3 | 31.4 | 32.4 | 34.6 | 36.2 | 33.8 | 33.9 |
| $C_3H_8$ | 9.98 | 19.1 | 6.73 | 15.0 | 6.1 | 4.0 | 4.1 | 14.3 | 8.9 | 8.0 | 8.4 | 4.9 | 5.02 |
| $C_4H_8$ | 10.8 | 6.19 | 8.82 | 7.28 | 0 | 8.56 | 6.36 | 13.8 | 12.1 | 13.2 | 13.8 | 0 | 11.2 |
| $C_4H_{10}$ | 1.99 | 1.14 | 1.63 | 1.35 | 0 | 1.58 | 1.17 | 2.55 | 2.24 | 2.44 | 2.55 | 0.95 | 2.06 |
| $C_5+$ | 4.51 | 7.32 | 2.41 | 1.42 | 0 | 1.01 | 2.09 | 4.64 | 3.90 | 5.19 | 4.58 | 0 | 3.12 |
| $C_2= C_3=$ Selectivity (wt %) | 68.3 | 51.2 | 77.1 | 58.1 | 9.2 | 81.7 | 81.2 | 61.0 | 70.6 | 69.1 | 68.7 | 80.3 | 76.5 |
| Lifetime (min.) | 40 | 45 | 51 | 170 | 33 | 32 | 37 | 66 | 65 | 56 | 65 | <2 | 36 |

TABLE 3

Metal Ions Modification on SAPO-34B-200.

| Metal | 34/A | Al— | Fe— | Co— | Ni— | Cu— | Zn— | Cr— | Mg— | Ca— | Ba— | Ti— | La— |
|---|---|---|---|---|---|---|---|---|---|---|---|---|---|
| Relative Crystallinity (%) | 100 | 69 | 30 | 25 | 59 | 65 | 0 | 69 | 68 | 21 | 6 | 7 | 14 |
| Reaction Conditions | | | | | | | | | | | | | |
| Reaction Temp. (° C.) | 460 | 455 | 450 | 450 | 450 | 450 | 450 | 450 | 455 | 455 | 455 | 455 | 450 |
| Reaction Time (min.) | 2.3 | 2 | 2 | 2 | 2 | 2 | 2 | 2 | 2 | 2 | 2 | 2 | 2 |
| Conversion (%) | 100 | 100 | 100 | 100 | 100 | 100 | 100 | 100 | 100 | 100 | 100 | 100 | 100 |
| Product Distribution (wt %) | | | | | | | | | | | | | |
| $CH_4$ | 0.63 | 0.73 | 0.87 | 3.26 | 65.5 | 4.96 | 0.93 | 0.72 | 0.69 | 0.82 | 1.11 | 8.31 | 0.78 |
| $C_2H_4$ | 37.1 | 42.7 | 45.0 | 44.7 | 14.7 | 65.4 | 47.7 | 43.3 | 41.6 | 38.4 | 32.6 | 43.0 | 37.5 |
| $C_2H_6$ | 0.38 | 0.39 | 0.59 | 1.06 | 10.8 | 9.07 | 0.23 | 0.57 | 0.48 | 0.37 | 0.28 | 0.37 | 0.31 |
| $C_3H_6$ | 40.2 | 39.6 | 38.1 | 29.9 | 6.41 | 19.4 | 39.5 | 38.9 | 39.2 | 43.0 | 46.5 | 38.3 | 43.1 |
| $C_3H_8$ | 3.04 | 2.11 | 4.63 | 4.94 | 1.93 | 0 | 0 | 4.62 | 4.54 | 3.66 | 3.98 | 0 | 4.10 |
| $C_4H_8$ | 11.9 | 9.79 | 8.30 | 9.60 | 0.70 | 1.04 | 7.61 | 8.47 | 9.59 | 9.30 | 9.72 | 7.62 | 9.97 |
| $C_4H_{10}$ | 2.19 | 1.80 | 1.53 | 1.78 | 0.01 | 0.19 | 1.41 | 1.56 | 1.77 | 1.72 | 1.80 | 1.41 | 1.84 |
| $C_5+$ | 4.02 | 2.83 | 0.97 | 4.78 | 0 | 0 | 2.55 | 1.84 | 2.16 | 2.71 | 4.02 | 0.95 | 2.41 |
| $C_2= C_3=$ Selectivity (wt %) | 77.2 | 82.4 | 83.1 | 74.6 | 21.1 | 84.7 | 87.3 | 82.2 | 80.8 | 81.4 | 79.1 | 81.3 | 80.6 |
| Lifetime (min.) | 210 | 143 | 32 | 35 | 33 | 31 | 32 | 32 | 62 | 30 | 34 | 34 | 61 |

TABLE 4

Metal Ions Modification on SAPO-34B-180.

| Metal | 34/A | Al— | Fe— | Co— | Ni— | Cu— | Zn— | Cr— | Mg— | Ca— | Ba— | Ti— | La— |
|---|---|---|---|---|---|---|---|---|---|---|---|---|---|
| Relative Crystallinity (%) | 100 | 80 | 64 | 40 | 68 | 72 | 50 | 46 | 94 | 47 | 36 | 44 | 7 |
| Reaction Conditions | | | | | | | | | | | | | |
| Reaction Temp. (° C.) | 460 | 450 | 450 | 455 | 450 | 450 | 445 | 447 | 452 | 445 | 450 | 452 | 450 |
| Reaction Time (min.) | 2.3 | 2 | 2 | 2 | 2 | 2 | 2 | 2 | 2 | 2 | 2 | 2 | 2 |
| Conversion (%) | 100 | 100 | 100 | 100 | 100 | 100 | 100 | 100 | 100 | 100 | 100 | 79.9 | 100 |
| Product Distribution (wt %) | | | | | | | | | | | | | |
| $CH_4$ | 0.63 | 0.56 | 0.65 | 2.16 | 8.57 | 5.34 | 2.05 | 0.72 | 0.57 | 0.63 | 0.70 | 40.8 | 1.00 |
| $C_2H_4$ | 37.1 | 38.1 | 44.9 | 44.7 | 47.6 | 68.3 | 57.0 | 38.6 | 40.8 | 37.6 | 35.4 | 31.9 | 39.4 |
| $C_2H_6$ | 0.35 | 0.43 | 0.54 | 0.71 | 2.30 | 6.87 | 0.79 | 0.57 | 0.55 | 0.37 | 0.26 | 1.55 | 1.07 |
| $C_3H_6$ | 40.2 | 41.2 | 39.7 | 38.5 | 31.5 | 18.5 | 30.5 | 40.8 | 39.0 | 42.1 | 45.4 | 18.9 | 33.8 |
| $C_3H_8$ | 3.04 | 4.80 | 4.67 | 3.79 | 2.87 | 0 | 2.92 | 5.32 | 5.14 | 4.90 | 3.76 | 1.40 | 5.45 |
| $C_4H_8$ | 11.9 | 10.4 | 8.04 | 8.49 | 6.06 | 0.89 | 5.71 | 10.1 | 10.0 | 10.1 | 9.60 | 4.60 | 11.7 |
| $C_4H_{10}$ | 2.19 | 1.92 | 1.49 | 1.57 | 1.12 | 0.17 | 1.05 | 1.87 | 1.84 | 1.87 | 1.75 | 0.85 | 2.15 |
| $C_5+$ | 4.02 | 2.24 | 0 | 0 | 0 | 0 | 0 | 2.02 | 2.11 | 2.47 | 3.06 | 0 | 2.47 |
| $C_2={C_3}=$ Selectivity (wt %) | 77.2 | 79.6 | 84.6 | 83.3 | 79.1 | 86.7 | 87.4 | 79.4 | 79.8 | 79.6 | 80.5 | 50.8 | 73.2 |
| Lifetime (min.) | 210 | 96 | 120 | 32 | 32 | 31 | 33 | 57 | 95 | 61 | 67 | <2 | 30 |

TABLE 5

Metal Ions Modification on M-34B-160.

| Metal | 34/A | Al— | Fe— | Co— | Ni— | Cu— | Zn— | Cr— | Mg— | Ca— | Ba— | Ti— | La— |
|---|---|---|---|---|---|---|---|---|---|---|---|---|---|
| Relative Crystallinity (%) | 100 | 94 | 63 | 82 | 93 | 75 | 93 | 66 | 97 | 68 | 70 | 50 | 5 |
| Reaction Conditions | | | | | | | | | | | | | |
| Reaction Temp. (° C.) | 460 | 450 | 450 | 450 | 448 | 450 | 450 | 450 | 450 | 450 | 450 | 450 | 450 |
| Reaction Time (min.) | 2.3 | 2 | 2 | 2 | 2 | 2 | 2 | 2 | 2 | 2 | 2 | 2 | 2 |
| Conversion (%) | 100 | 100 | 100 | 100 | 100 | 100 | 100 | 100 | 100 | 100 | 100 | 100 | 100 |
| Product Distribution (wt %) | | | | | | | | | | | | | |
| $CH_4$ | 0.63 | 0.59 | 0.64 | 1.03 | 4.99 | 2.30 | 1.21 | 0.67 | 0.59 | 0.53 | 0.75 | 4.57 | 1.12 |
| $C_2H_4$ | 37.1 | 37.3 | 41.4 | 42.3 | 42.3 | 66.0 | 52.5 | 40.4 | 39.3 | 39.0 | 34.4 | 45.3 | 40.0 |
| $C_2H_6$ | 0.38 | 0.52 | 0.52 | 0.53 | 1.53 | 2.91 | 0.52 | 0.52 | 0.47 | 0.34 | 0.30 | 2.00 | 1.02 |
| $C_3H_6$ | 40.2 | 40.5 | 39.9 | 38.3 | 35.1 | 20.7 | 35.3 | 41.3 | 40.3 | 44.3 | 43.9 | 30.9 | 35.5 |
| $C_3H_8$ | 3.04 | 6.24 | 5.14 | 4.05 | 4.13 | 1.56 | 2.78 | 3.93 | 4.90 | 3.96 | 4.12 | 7.19 | 4.41 |
| $C_4H_8$ | 11.9 | 10.9 | 9.14 | 9.38 | 8.08 | 5.49 | 6.25 | 9.52 | 10.36 | 8.53 | 11.44 | 8.55 | 12.03 |
| $C_4H_{10}$ | 2.19 | 2.00 | 1.69 | 1.77 | 1.49 | 1.02 | 1.16 | 1.76 | 1.92 | 1.57 | 2.11 | 1.58 | 2.22 |
| $C_5+$ | 4.02 | 2.00 | 1.55 | 2.50 | 2.41 | 0 | 0.33 | 1.93 | 1.77 | 1.83 | 2.47 | 0 | 3.78 |
| $C_2=C=$ Selectivity (wt %) | 77.2 | 77.8 | 81.3 | 80.5 | 77.4 | 86.7 | 87.8 | 81.7 | 79.7 | 83.2 | 78.3 | 76.1 | 75.4 |
| Lifetime (min.) | 210 | 97 | 61 | 67 | 31 | 30 | 40 | 65 | 79 | 71 | 96 | 28 | 33 |

What is claimed is:

1. A method of making a molecular sieve comprising:
   a) mixing a metal containing solution with a silicoaluminophosphate molecular sieve, wherein the silicoaluminophosphate molecular sieve contains a template;
   b) heating the mixture to a temperature between 30° C. and 400° C. to obtain a silicoaluminophosphate molecular sieve having a surface heat impregnated with a metal;
   c) separating the heated silicoaluminophosphate molecular sieve from the heated metal containing solution; and
   d) calcining the separated silicoaluminophosphate molecular sieve.

2. The method of claim 1 wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and mixtures thereof.

3. The method catalyst of claim 1 wherein the silicoaluminophosphate molecular sieve is selected from the group consisting of SAPO-18, SAPO-34, SAPO-35, SAPO-44, SAPO-47, and mixtures thereof.

4. The method of claim 3 wherein the silicoaluminophosphate molecular sieve is selected from the group consisting of SAPO-34A, SAPO-34B, and mixtures thereof.

5. The method of claim 1 wherein the calcined silicoaluminophosphate molecular sieve comprises 0.5 to 40 percent by weight of the metal.

6. The method of claim 5 wherein the calcined silicoaluminophosphate molecular sieve comprises 1 to 20 percent by weight of the metal.

7. The method of claim 6 wherein the calcined silicoaluminophosphate molecular sieve comprises 1 to 10 percent by weight of the metal.

8. The method of claim 1 wherein the metal is selected from the group consisting of Group IIA metals, Group IIIA metals, Group IB metals, Group IIB metals, Group IIIB metals, Group VIB metals, Group VB metals, Group VIB metals, Group VIIB metals, Group VIIIB metals, and mixtures thereof.

9. The method of claim 1 wherein the metal is selected from the group consisting of aluminum, magnesium, calcium, barium, lanthanum, titanium, chromium, iron, cobalt, nickel, copper, zinc, and mixtures thereof.

10. The method of claim 9 wherein the metal is copper, zinc, or a mixture thereof.

11. The method of claim 1 wherein the metal is a heat decomposition product of a metal acetate, metal nitrate, metal sulfate, or metal halide.

12. The method of claim 11 wherein the surface is heat impregnated with the metal at a temperature from 120° C. to 260° C.

13. The method of claim 12 wherein the surface is heat impregnated with the metal at a temperature from 160° C. to 220° C.

14. The method of claim 1 wherein the mixture is heated at autogeneous pressure.

15. The method of claim 1 wherein the metal containing solution has a metal concentration between 0.01 M and 1.0 M.

16. The method of claim 15 wherein the metal containing solution has a metal concentration between 0.05 M and 0.5 M.

17. The method of claim 16 wherein the metal containing solution has a metal concentration between 0.08 M and 0.3 M.

18. The method of claim 1 wherein the metal containing solution comprises metal salts selected from the group consisting of acetates, nitrates, sulfates, halides, and mixtures thereof.

* * * * *